United States Patent [19]

Sundström, deceased et al.

[11] Patent Number: 5,713,737
[45] Date of Patent: Feb. 3, 1998

[54] RUBBER DAM CLAMP

[76] Inventors: Folke Sundström, deceased, late of Djursholm; by Kerstin Sundström, heir; by Carl Johan Torsten Sundström, heir, both of Burevägen 7, S-182 63 Djursholm; by Karin Emma Sofia Sundström, heir; by Mets Gustaf A. Sundström, heir, both of Aminnevägen 15, S-104 05 Stockholm, all of Sweden

[21] Appl. No.: 532,588
[22] PCT Filed: Apr. 6, 1994
[86] PCT No.: PCT/SE94/00305
  § 371 Date: Sep. 26, 1995
  § 102(e) Date: Sep. 26, 1995
[87] PCT Pub. No.: WO94/22388
  PCT Pub. Date: Oct. 13, 1994

[30] Foreign Application Priority Data

Apr. 6, 1993 [SE] Sweden ............... 9301134

[51] Int. Cl.[6] ................................................ A61C 5/12
[52] U.S. Cl. ................................................ 433/139
[58] Field of Search .......................... 433/39, 137, 138, 433/139, 148

[56] References Cited

U.S. PATENT DOCUMENTS

| | | | |
|---|---|---|---|
| 1,532,821 | 4/1925 | Ivory | 433/139 |
| 4,265,623 | 5/1981 | Soelberg et al. | 433/139 |
| 4,661,063 | 4/1987 | Levy | 433/139 |
| 4,787,849 | 11/1988 | Jacoby et al. | 433/139 |

FOREIGN PATENT DOCUMENTS 452537  5/1913  France ............... 433/139

*Primary Examiner*—Cary E. O'Connor
*Attorney, Agent, or Firm*—Fasth Law Firm

[57] ABSTRACT

The rubber dam clamp is made of fiber-reinforced plastic. The dam clamp has a pair of gripping claws that are adapted to engage a tooth neck. A resilient bridge connects the gripping claws. A pair of open sockets are defined in an inside of the gripping claws between the bridge and the gripping claws. The sockets are adapted to receive the points of a rubber dam clamp forceps so that the dam clamp may be opened without the risk of the forceps being caught in the socket when the dam clamp is released and the forceps is to be removed therefrom.

13 Claims, 1 Drawing Sheet

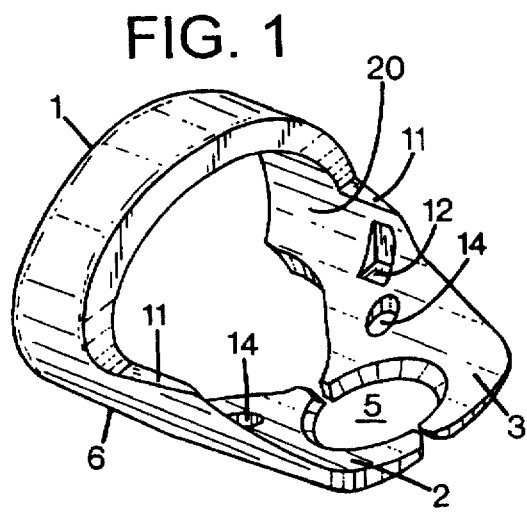
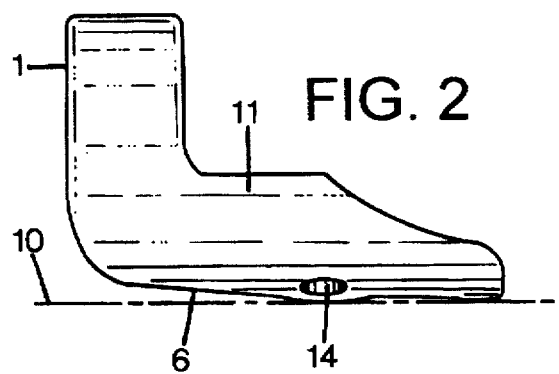
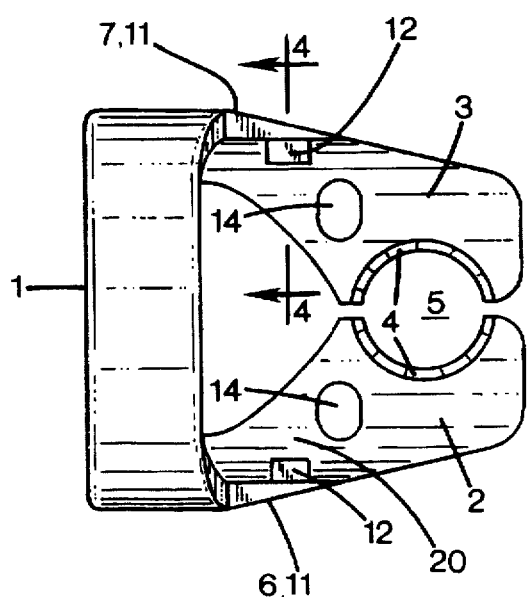
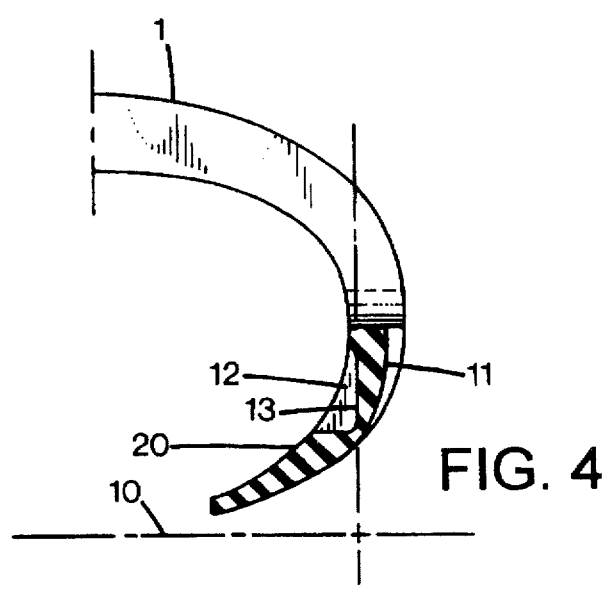

RUBBER DAM CLAMP

TECHNICAL FIELD

The invention relates to a rubber dam clamp, that is to say a clamp which is used by dentists as an aid for securing a so-called rubber dam sheet on the teeth and which for this purpose has a pair of gripping claws, intended to engage against a tooth neck, and a resilient bridge which connects the gripping claws.

BACKGROUND TO THE INVENTION

The purpose of the rubber dam sheet is to isolate the field of operation on the teeth from saliva, blood and respiratory air, but also to prevent chemicals, filling material etc. from coming into contact with mucous membranes and the throat. Rubber dams have been used at least since the 1920s, and most of the associated aids have changed little since then. The rubber dam clamps which are used to secure the sheet on the teeth have hitherto been made of metal and are available in a large number of sizes and shapes. They consist of a single or double resilient bridge and of gripping claws which will engage against the tooth neck and which for this purpose are shaped in accordance with the anatomy of the tooth necks. The clamps are stiff and must be applied and removed using special forceps, with points, which are fitted into forceps sockets in the form of holes in the area of the gripping claws.

The rubber dam clamps made of metal have a number of disadvantages. In addition to the fact that they are relatively expensive and to a large extent absorb X-radiation, it should also be noted that considerable force is required when applying and removing them, they are felt to be uncomfortable by the patients ("iron grip"), and the metal edges cause a greater or lesser amount of damage to the tooth necks. When the clamps are stretched out to a large degree, the fixture holes for the forceps are often positioned obliquely in relation to the jaws of the forceps, with the result that it can be extremely difficult to remove the forceps and even more difficult to stick the points of the forceps into the holes when the clamp is to be removed.

BRIEF DISCLOSURE OF THE INVENTION

The object of the invention is to eliminate the abovementioned disadvantages and at the same time to offer further advantages, and this can be achieved by virtue of the fact that the invention is characterized by what is stated in the patent claims which follow.

It is expedient that the basic shape of the rubber dam clamp according to the invention should correspond to that of conventional rubber dam clamps made of metal so that it will be compatible with existing rubber dam forceps and other aids. However, the use of fibre-reinforced plastic, which is proposed preferably as the material for the rubber dam clamps in place of metal, affords considerable possibilities for variations in the design. Thus, the clamp can and should be given varying material thickness in different parts of the clamp in order thereby to obtain an optimal combination of spring power, manageability, gripping capacity etc. To this end, the bridge is preferably given a greater material thickness than, for example, the claws.

By means of a suitable material distribution it is also possible, in accordance with a preferred embodiment, to make the clamp more elongate than conventional rubber dam clamps made of metal, as a result of which the rubber dam sheet can be better held away distally from the tooth, so that the dentist has more room for the instruments.

In addition to closed sockets in the form of holes for the rubber dam forceps, or as an alternative to these, open sockets for the forceps are arranged, according to the invention, on the inner side of transition areas between the bridge and each gripping claw. These open sockets for the forceps can comprise parts of the said transition areas, the surface against which the forceps are pressed in the respective forceps socket extending in a plane which is essentially at right angles with respect to a base plane, which is defined by the inner edge of the gripping claws. More specifically, these open sockets for the forceps are expediently given the form of groove-shaped recesses in the inner sides, facing each other, of the transition areas. According to a preferred embodiment these recesses extend in a direction essentially at right angles with respect to the base plane. By using these open sockets for the forceps, there is never any risk, for the dentist, of the forceps becoming stuck.

According to another possible embodiment, the open sockets for the forceps consist of essentially T-shaped recesses, with the horizontal part of the forceps socket being parallel to and directed towards the said base plane, and the forceps intended for use with these recesses having points which are shaped so as to fit into these recesses.

The technique for producing the rubber dam clamp according to the invention also involves such low production costs that the rubber dam clamp can be used as a throw-away article. It is also possible for the dentist himself, using a file or a rotary grinding tool, for example a small grinding wheel in a dental drill machine, to cut out a suitable shape for the inner edge of the gripping claws, so that this edge is adapted to the tooth neck in question. In this way it is possible in each situation to achieve a very good contact with the tooth, and at the same time the number of shapes and sizes of the rubber dam clamps kept in store can be reduced.

Another advantage of rubber dam clamps having a plastic matrix is that the rubber dam sheet can be more easily secured to the clamp, expediently by gluing or welding.

Plastics which can be used as the material for the rubber dam clamps according to the invention include a number of thermoplastics. Some polyamide plastics are especially suitable, and in particular nylon-12. Acetal plastic (polymerized formaldehyde, POM) can also be used. A copolymer thereof with a small quantity of ethylene oxide or dioxane is also possible.

Among suitable fibres there may be mentioned, in the first instance, glass fibres of micro size, which is here understood to mean lengths of less than one millimetre. The glass fibres can preferably have a length of the order of magnitude of "a tenth of a millimetre or so", which can also be expressed by saying that most of the glass fibres (of the total volume or mass of the fibres) will have a length within the range from 0.05 to 0.5 mm. The plastic should expediently contain 20–60% by weight of glass fibres, preferably 30–50% by weight. Among other possible fibres which can be used as a reinforcement for the material, carbon fibres may be mentioned. If carbon fibres are used instead of glass fibres, a smaller quantity can give the same reinforcing effect. Mineral fibres, fibres of organic material etc. are also possible, in principle, as the ingredient for reinforcing the plastic matrix.

Further characteristics and aspects of the invention will emerge from the following patent claims and from the description, given below, of a possible embodiment of a rubber dam clamp made of plastic according to the invention.

BRIEF DESCRIPTION OF THE FIGURES

In the following description of a possible embodiment, reference will be made to the attached drawing, in which:

FIG. 1 shows, on an enlarged scale, a perspective view of a rubber dam clamp made of plastic according to the invention.

FIG. 2 shows the same rubber dam clamp from one side.

FIG. 3 shows the rubber dam clamp from above, and

FIG. 4 shows a part of the rubber dam clamp in a section through IV—IV in FIG. 3. on an even larger scale.

DESCRIPTION OF A PREFERRED EMBODIMENT

The rubber dam clamp shown in the figures of the drawing is produced, according to the preferred embodiment, by injection moulding of nylon-12 containing 40% by weight of glass fibres, with most of the fibres being in the length range from 0.05 to 0.5 mm. The clamp consists of a resilient bridge 1, a pair of claws 2, 3, the inner bevelled edges 4 of which form a grip 5, and, between the resilient bridge 1 and the claws 2, 3, a pair of transition areas 6, 7. The latter are more elongate than corresponding parts of conventional rubber dam clamps made of metal and can be described as legs protruding from the bridge 1, which legs end with the inwardly directed gripping claws 2, 3, the inner edge 4 of which defines a base plane 10. Despite the considerable length of the transition areas/legs 6, 7, the necessary spring force can be transmitted from the bridge 1 to the gripping claws 2, 3 by virtue of the fact that the transition areas 6, 7 are given an apposite material thickness adapted to the moments which may arise during the use of the rubber dam clamp. The bridge 1 itself is also normally given a relatively large wall thickness in order to provide a corresponding spring force, while the gripping claws 2, 3 are designed narrowing towards the edge 4 so that the desired gripping effect against the tooth neck is obtained.

In each of the transition areas 6, 7 there is an upper part 11 which adjoins the bridge 1. On inner side 20 of these two opposite upper parts 11 there is a recess 12 which is in the form of a groove which is essentially vertical in relation to the base plane 10, when the latter is horizontal. The design of such a groove 12 is shown in FIG. 4. However, the grooves can have another direction or design, especially if a rubber dam forceps other than the conventional one is to be applied. The two grooves 12 function as open sockets for the points of a rubber dam clamp forceps, which is applied against the inner wall 13 in the respective groove 12. This inner wall 13 extends in the vertical direction, that is to say in a direction at right angles with respect to the base plane 10.

Between the two open forceps sockets 12 and the gripping claws 2, 3 there is also a pair of closed forceps sockets of conventional design in the form of through-holes 14.

It is claimed:

1. Rubber dam clamp having a pair of gripping claws (2, 3), intended to engage against a tooth neck, and a resilient bridge (1) which connects the gripping claws, each gripping claw having a thickness and an inner side disposed between the resilient bridge and the gripping claws so that each inner side is facing one another, each inner side having an open socket defined therein adapted to receive points of a rubber dam clamp forceps, the open sockets facing towards one another, the rubber dam clamp being made of a fiber reinforced material, the resilient bridge having a thickness that is greater than the thickness of the gripping claws, the sockets having an inner surface facing one another so that the sockets are partially defined by the inner surfaces and bottom surfaces.

2. Rubber dam clamp according to claim 1 wherein a substantially round opening is formed by the gripping claws when the gripping claws are adjacent one another.

3. Rubber dam clamp having a pair of gripping claws having a thickness, intended to engage against a tooth neck, and a resilient bridge which connects the gripping claws, each gripping claw having an inner side disposed between the resilient bridge and the gripping claws so that each inner side is facing one another, each inner side having an open socket defined therein adapted to receive points of a rubber dam clamp forceps, the open sockets facing towards one another, the rubber dam clamp being made of a fiber reinforced material, the resilient bridge having a thickness that is greater than the thickness of the gripping claws, the open forceps sockets (12) are defined in upper parts (11) of transition areas (6, 7), the inner surface (13) against which the forceps point is pressed into the respective socket (12) extending in a plane which is essentially at right angles with respect to a base plane (10), which is defined by the inner edge (4) of the gripping claws.

4. Rubber dam clamp according to claim 3, characterized in that the said open forceps sockets (12) are formed by groove-shaped recesses in the inner sides, facing each other, of the transition areas, which recesses extend at least partially in a direction essentially at right angles with respect to the base plane (10).

5. Rubber dam clamp according to claim 4, wherein each socket is defined by an inner wall and a base plane, the inner wall is perpendicular to the base plane.

6. Rubber dam clamp according to claim 3, characterized in that the open forceps sockets (12) are arranged between the bridge (1) and closed forceps sockets (14), in the form of through-holes in the two gripping claims (2, 3).

7. Rubber dam clamp according to claim 3, wherein the rubber dam clamp comprises a polyamide plastic.

8. Rubber dam clamp according to claim 7, wherein the polyamide plastic is acetal.

9. Rubber dam clamp according to claim 7 wherein the plastic contains 30–50% by weight of glass fibres.

10. Rubber dam clamp according to claim 7, characterized in that the plastic contains 20–60% by weight of fibres.

11. Rubber dam clamp according to claim 3, characterized in that the fiber reinforced material consists of glass fibres.

12. Rubber dam clamp according to claim 11 characterized in that most of the fiber reinforced material comprises fibres that have a length of between 0.05 and 0.5 mm.

13. Rubber dam clamp according to claim 12 wherein the fibres consist of carbon fibres.

* * * * *